United States Patent
Nilsson

(12) 
(10) Patent No.: US 6,592,930 B2
(45) Date of Patent: Jul. 15, 2003

(54) PARTICLE FLOW CONTROL

(75) Inventor: Thomas Nilsson, Mariefred (SE)

(73) Assignee: Microdrug AG, Hergiswil (CH)

( * ) Notice: Subject to any disclaimer, the term of this patent is extended or adjusted under 35 U.S.C. 154(b) by 0 days.

(21) Appl. No.: 09/928,443

(22) Filed: Aug. 14, 2001

(65) Prior Publication Data

US 2003/0012865 A1 Jan. 16, 2003

(30) Foreign Application Priority Data

Jul. 13, 2001 (SE) .............................. 0102518

(51) Int. Cl.$^7$ .............. B05D 1/04; B05D 1/06

(52) U.S. Cl. .............. 427/2.14; 427/2.1; 427/458; 427/466; 427/468; 427/469; 427/472; 427/473; 427/282

(58) Field of Search ................ 427/2.1, 2.14, 427/458, 466, 468, 469, 472, 473, 282

(56) References Cited

U.S. PATENT DOCUMENTS 6,007,630 A * 12/1999 Pletcher et al. ............. 118/621

* cited by examiner

*Primary Examiner*—Shrive P. Beck
*Assistant Examiner*—Jennifer Kolb Michener
(74) *Attorney, Agent, or Firm*—Young & Thompson

(57) ABSTRACT

A method and a device involving an electric iris diaphragm/shutter are disclosed for controlling particle transfer of electrically charged medication powder particles from a source to a defined target area, of a substrate. Spatial distribution of particles onto the target area is achieved by an electro-dynamic field technique (320) applied to the distribution and deposition of particles in a dose forming process. An electric iris diaphragm/shutter (130) is located between a particle generator (110) and the substrate (140) such that all particles must pass the iris diaphragm for being transferred to the substrate. By adjusting amplitude and frequency of a superimposed AC potential (136) charged particles will oscillate in the created AC field such that only small light particles will emerge from the iris diaphragm/shutter for further transfer in the dose forming process.

11 Claims, 11 Drawing Sheets

PARTICLE FLOW CONTROL

TECHNICAL FIELD

Figure 1:
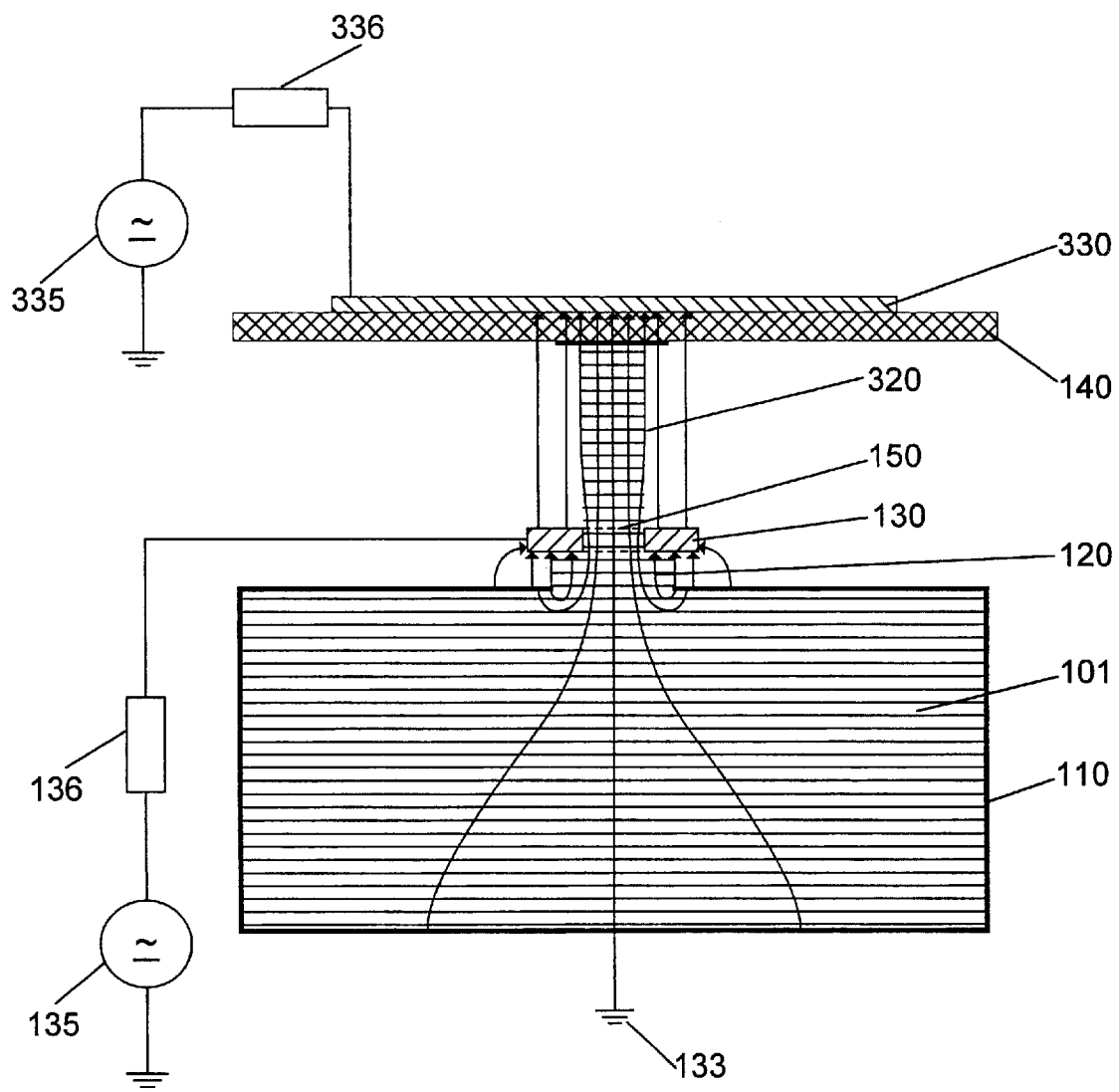

The present invention relates to a method and a device for controlling the flow and spatial distribution of dry medication powder being deposited on a substrate in a dose forming process, and more specifically by using an electric iris diaphragm/shutter (a diaphragm which is also operable as a shutter) in forming pre-metered doses particularly of finely divided dry medication electro powder.

BACKGROUND

The dosing of drugs is carried out in a number of different ways in the medical service today. Within health care there is a rapidly growing interest in the possibility of acting dosing systemic medication drugs as a powder directly to the airways and lungs of a patient by means of an inhaler in order to obtain an effective, quick and user-friendly administration of such substances.

A dry powder inhaler, DPI, represents a device intended for administration of powder into the deep or upper lung airways by oral inhalation. For systemic delivery of medication drugs a deep lung deposition is used, but for local treatment of the airways the objective is local deposition, not deep lung. With deep lung should be understood the peripheral lung and alveoli, where direct transport of active substance to the blood can take place. In order for a particle to reach into the deep lung the aerodynamic particle size should typically be less than 3 $\mu$m, and for a local lung delivery typically less than 5 $\mu$m. Larger particle sizes will easily stick in the mouth and throat, which underlines the importance of keeping the particle size distribution of the dose within tight limits to ensure that a high percentage of the dose actually is deposited in the deep lung upon inhalation when the objective is systemic delivery of a drug. Furthermore, the inspiration must take place in a calm manner to decrease air speed and thereby reduce deposition in the upper respiratory tracts.

To succeed with systemic delivery of medication powders to the deep lung by inhalation there are some criteria, which have to be fulfilled. It is for instance very important to obtain a high dosing accuracy in each administration to the user. A very high degree of de-agglomeration of the medication powder is also of great importance. This is not possible with dry powder inhalers of today without special arrangements as for example a so-called spacer.

Powders for inhalers have a tendency of agglomerating, in other words to clod or to form smaller or larger lumps, which then have to be de-agglomerated. De-agglomeration is defined as breaking up agglomerated powder by introducing electrical, mechanical, or aerodynamic energy. Usually de-agglomeration is performed in at least two stages: stage one is in the process of depositing powder while building up the dose and stage two is in the process of dispersing the powder during the patient's inspiration of air through the DPI.

The term electro-powder refers to a finely divided medication powder presenting controlled electric properties being suitable for administration by means of an inhaler device. Such an electro-powder provides possibilities for a better dosing from equipment using a technique for electric field control such as disclosed in our U.S. Pat. No. 6,089,227 as well as our Swedish Patents No. 9802648-7 and 9802649-5, which present excellent inhalation dosing performance. The state of the art also discloses a number of solutions for depositing powder for dosing. The International Application WO 00/22722 presents an electrostatic sensing chuck using area matched electrodes. U.S. Pat. No. 6,063,194 discloses a powder deposition apparatus for depositing grains on a substrate using an electrostatic chuck having one or more collection zones and using an optical detection for quantifying the amount of grains deposited. U.S. Pat. Nos. 5,714,007 and 6,007,630 disclose an apparatus for electrostatically depositing a medication powder upon predefined regions of a substrate, the substrates being used to fabricate suppositories, inhalants, tablet capsules and the like. In U.S. Pat. Nos. 5,699,649 and 5,960,609 are presented metering and packaging methods and devices for pharmaceuticals and drugs, the methods using electrostatic photo technology to package microgram quantities of fine powders in discrete capsule and tablet form.

A common difficulty encountered when using electrostatic technology and/or electrical fields in combination with electrostatic charging of the powder particles in a deposition process, is to remove the charge of the particles and the charge of the substrate, if an isolator, as the particles are being deposited on the substrate for forming the dose. If the removal of charges is incomplete or takes too long it will affect the forming of the dose negatively in that the charged particles already deposited will present a local repelling electric field, which tends to stop newly attracted particles from settling on the targeted area of the substrate and forces newcomers to settle at the outskirts of the target area. The repelling field grows in strength as more particles are deposited on the target area. Finally, the field is so strong that further deposition is not possible even if the net field strength at some distance from the target area is exerting an attractive force on the charged particles.

In cases where electrostatic chucks are used, regardless of whether the chuck substrate, normally of a dielectric material, is pre-charged in the deposition area or areas to create the necessary local electric field in the target area(s), or a system of electrodes are used to attract the charged particles or if a combination of pre-charging and electrodes are used, it is always difficult to fill the target area with the correct amount of particles, because the repelling field grows stronger with every particle deposited, leading to a spreading out of particles over a larger area than the intended target area. This is also true where the target area, the deposition area, is beads, which are captured and held by the chuck by for instance electrostatic force during the deposition of particles onto the beads themselves. It is thus often impossible to form doses of sufficient mass and suitable spatial shape. Often, the chuck principle also requires powders of predetermined or known specific charge ($\mu$C/g) in order to predict the mass of particles attracted to the chuck, which in itself presents a big challenge.

Further, prior art technology devices seldom reach a sufficiently high degree of de-agglomeration, and an exact dose with a low relative standard deviation (RSD) between doses is not well controlled. This is partly due to difficulties in controlling the production line parameters during production of the doses, partly due to shortcomings in the design of the inhaler device, which makes it hard to comply with regulatory demands. The difficulties leave much to be desired when it comes to dose conformity and lung deposition effectiveness of the medication substance. Therefore, there is still a demand for pre-fabricated high accuracy pre-metered doses to be loaded into an inhaler device, which then will ensure repeated and exact systemic or local pulmonary delivery of doses administered by inhalation.

SUMMARY

A method and a device are defined for controlling the transfer of charged particles of a medication powder emitted from a particle generator to a defined target area of a substrate in a dose forming process. A particle transfer electrode is arranged for forming an electric iris diaphragm and shutter with an electric field associated for the transfer of the powder particles from the particle generator to the defined target area of a substrate to carry a pre-metered powder dose, thereby to control the direction and speed of particles in the dose forming process. The electric iris diaphragm/shutter is located between the particle generator and the substrate such that all particles must pass the iris diaphragm for being transferred to the substrate. This iris diaphragm is also operating as a shutter. By adjusting amplitude and frequency of a superimposed AC potential charged particles will oscillate in the created AC field such that only small light particles emerge from the iris diaphragm/shutter for further transfer in the dose forming process. Furthermore by the adjustment of amplitude and frequency a majority of charged particles emerging are accelerated and retarded in synchronism with the AC field, such that they impact on a defined target area of the substrate with a low speed and momentum resulting in a desired dose porosity.

BRIEF DESCRIPTION OF THE DRAWINGS

The invention, together with further objects and advantages thereof, may best be understood by referring to the following detailed description taken together with the accompanying drawings, in which:

FIG. 1 illustrates in principle a first embodiment of an iris diaphragm/shutter comprising one electrode only, showing how charged particles are being transferred from the particle generator to the target area of the substrate member;

FIG. 2 illustrates the same embodiment as in FIG. 1 but with the transfer of particles inhibited by a repelling acting electric field from the electrode of the iris diaphragm/shutter;

FIG. 3 illustrates in principle a second embodiment of an iris diaphragm/shutter comprising two electrodes, showing how charged particles are transferred from the particle generator to the target area of the substrate member;

FIG. 4 illustrates a typical embodiment of an iris diaphragm/shutter comprising two electrodes;

FIG. 5 illustrates in principle a third embodiment of an iris diaphragm comprising four electrodes, showing how charged particles are transferred from the particle generator to the target area of the substrate member, which may be moved by a servo mechanism during dose forming;

FIG. 6 illustrates in principle one side of a typical iris diaphragm showing a second electrode;

FIG. 7 illustrates in principle one side of a typical iris diaphragm showing a first electrode;

FIG. 8 illustrates in principle an iris diaphragm with two electrodes, a dose being formed onto the target area of the substrate member and two ion sources for neutralizing accumulated charge in the dose being formed;

FIG. 9 illustrates in principle an iris diaphragm with two electrodes, a dose being formed onto the target area of the substrate member, a servo arrangement for moving the substrate member in relation to the iris and an ion source for neutralizing accumulated charge in the dose being formed;

FIG. 10 illustrates, taken together with FIG. 9, in principle a substrate member in the shape of a revolving cassette with more than one target area, doses being formed onto the target areas and an ion source for neutralizing—one by one—accumulated charge in the doses being formed;

FIG. 11 illustrates schematically a substrate member, an iris diaphragm, a dose in forming and an ion source positioned behind the substrate member connecting without physical contact the third voltage source with the third electrode; and FIG. 12 is a flow diagram illustrating the method of the present invention.

DESCRIPTION OF THE INVENTION

A method and a device involving an electric iris diaphragm are disclosed for controlling the particle transfer of electrically charged medication powder particles from a source to a defined area, the target area, of a substrate member. Spatial distribution of particles onto the target area or dose bed is achieved by means of electro-dynamic field technique applied to the distribution and deposition of particles in a dose forming process. The term "electro-dynamic field technique" in the context of this document refers to the effective electric field in four dimensions, space and time, resulting from well controlled—in terms of timing, frequency and amplitude—potentials applied to a number of electrodes placed in suitable positions in the space confined by a dose forming apparatus. The term "quasi-stationary electric field" is in this context used to describe an electric field or fields being controlled by voltage source devices with controlled impedances, all part of a control system, where the applied voltages may be controlled arbitrarily and individually in the low-frequency time-domain. To facilitate the understanding of where and how voltages are applied all voltages are assumed to be referenced to ground potential throughout this document. Naturally ground potential may be exchanged for an arbitrary potential when utilizing the invention. It will be apparent to a person skilled in the art that any singular potential or voltage may be referenced to another potential or voltage source, e.g. in order to simplify or improve a control system, without departing from the spirit and scope of the invention as defined by the appended claims.

A particle generator is provided, which either produces positively and/or negatively charged particles by corona-, tribo- or induction-charging. The charged particles are emitted from the generator into a controlled atmosphere, normally air, where they enter an electric field coming from suitably positioned electrodes at suitable potentials supplied by controlled voltages from suitable voltage sources. At least one of the electrodes comprises an electric iris diaphragm/shutter. The iris diaphragm/shutter has at least one aperture of suitable size and shape where particles can pass through and it is positioned between the particle generator and the substrate. The strength and direction of the composed electric field between the particle generator and the iris diaphragm depends on the size and shape of the electrodes used, their relative positions and not least on the potentials applied to the electrode or electrodes of the iris diaphragm as well as to the other electrodes. In this way, it is possible to control the electric forces acting on the charged particles, which are attracted to or repelled from parts or all of the iris diaphragm and its apertures. Charged particles passing through an aperture of the iris diaphragm enter a further applied electric field set up between ground, or any other electric reference, and an electrode supplied with a potential from a voltage source. The electrode is preferably positioned behind the substrate. Provided that the relative positions of the apertures and the target area are reasonably aligned, the charged particles leaving the iris diaphragm at this stage are captured by the field and attracted to the substrate and begin to travel in that direction along the field lines until they hit the target area of the substrate where they are deposited.

Two properties of the iris diaphragm/shutter are of particular importance. The first one is the ability to control the apparent size of the aperture or apertures of the electric iris diaphragm such that it appears smaller or larger to the attracted particles depending on what voltage potentials are applied to the electrodes. This opens the possibility to control the area of particle flow through the iris diaphragm and consequently the utilized area of the target area of the substrate member onto which the transported particles will be deposited. The second important property is that the electric iris diaphragm can be made to work as a particle flow control valve, i.e. a shutter arrangement, such that it is possible to switch the flow of particles completely on or off by simply feeding suitable voltages to the electrodes, which will turn the composite electric field in the opposite direction then forcing charged particles away from the iris diaphragm. In fact, by adjusting the voltages suitably, it is also possible to partly control the amount of particles per unit time that are let through and in this manner trim the particle deposition rate on the target area. In a preferred embodiment, however, the iris diaphragm is mainly used for area size control and switching the flow on or off instantly.

Further, the electric iris diaphragm may be used to screen the particles such that only small particles of preferred sizes are let through. This is achieved by superimposing an alternating AC field on the composite quasi-stationary electric field of the iris diaphragm. The working principle is based on the moment of inertia, whereby large particles have much more mass than small ones but less charge per unit weight so that the former accelerate much more slowly in a given field compared to the latter. If the frequency of the AC field is suitable, the large particles will never come through the iris diaphragm, but may stay beneath until they lose their charge so that e.g. the force of gravitation can bring them to a collection zone. These particles may then be further de-agglomerated and fed to the particle generator and re-introduced in the dose forming process.

In a typical embodiment, the iris diaphragm comprises two electrodes with a thin isolating wafer member between them, and a single aperture through the iris diaphragm. The electrodes and the isolating wafer member are typically made as a printed circuit board (PCB) having a topside and a bottom side. The electrode (topside by definition) closest to the substrate member is typically circular in shape and concentric with the aperture, while the other electrode (bottom-side by definition) is closest to the particle generator and may cover the lower side of the PCB completely. In a preferred embodiment, the substrate member is positioned upside down above the particle generator such that the net electrostatic force acting on emitted charged particles is directed upwards counteracting the force of gravity during forming of the dose. In this manner no big or heavy particles can land on the target area by accident under the influence of gravity alone. The potentials applied to the electrodes of the iris diaphragm are controlled by a control system, which is not part of the invention. The potentials are preferably varied in a determined way during the course of the dose forming process such that the dose obtains the intended properties. While the transfer of particles takes place from the generator through the iris diaphragm to the target area of the substrate member the potential fed to the top electrode is typically a few hundred volts, positive or negative, in order to attract charged particles. The electrode on the bottom side is typically fed with a potential between zero and some tens of volts in order to slightly repel the charged particles and help guiding particles through the iris diaphragm. The particles emerging from the aperture topside of the iris diaphragm enter the attracting field emanating from the electrode behind the target area of the substrate member. The attracting electrode is typically fed with a potential between 500 and 2000 V. The emerging particles therefore continue on their path in the direction of the target area. During the dose forming process the transfer of particles may be interrupted by the control system, which may create a strong repelling electric field within the iris diaphragm by feeding suitable opposing potentials to the electrodes such that no charged particles can penetrate the aperture of the iris diaphragm.

The prior art limitations in total dose mass and bad spatial control of the dose layout are eliminated by fast and efficient removal of charges from the charged powder particles and from the target area of the substrate, i.e. the dose bed, thus eliminating the repelling field from the dose during forming. Very quick neutralization will be achieved, e.g. by arranging an ion-generator near the substrate such that the emitted ions are directed towards the dose and the target area of the substrate. The emitted ions ionize the air and the resulting oxygen and nitrogen ions of both positive and negative charge may be attracted to the dose and the substrate, whereby some of them will hit the dose and the substrate and recombine, neutralizing the accumulated charges in the process. By immediate neutralization of the particle charge once the particle has been deposited on the substrate the negative influence from the particle charge on incoming particles is eliminated. The spatial deposition of the particles is thus vastly improved with no particles settling outside the target area, because the sum of charges at the dose bed and the dose being formed as a whole is continuously neutralized in this way eliminating a distorting, repelling electric field from arising. In a typical embodiment of the invention the accumulated charge within the dose and dose bed is regularly neutralized during the dose forming process as described. The relevant target area of the substrate member is brought within the range of an ion-generator by a servo mechanism, such that the accumulated charge is neutralized at least once and more preferably at least three times during the forming of the dose. It is also typical that the substrate member must pass by the ion-generator to neutralize any residual charge from the target area before commencing a dose forming operation.

The basic principle of the method according to the present invention is illustrated in FIG. 1.

The method utilizes electro-dynamic field technique in order to screen particles;

transport particles;

distribute particles over a pre-defined area on a substrate member;

deposit particles onto a pre-defined area on a substrate member;

control the mass of the dose being formed;

switch the particle flow on or off as function of time, and control the porosity of the dose Further, the method is based on externally applied electric fields into which the charged particles are introduced. In a preferred embodiment, electro-powder is used, but other powders may be possible to use, which is easily recognized by people of ordinary skill in the art.

The electro-powder forms an active dry powder substance or dry powder medication formulation with a fine particle fraction (FPF) presenting of the order 50% or more of the powder mass with an aerodynamic particle size below 5 $\mu$m and provides electrostatic properties with an absolute specific charge per unit mass of the order 0.1 to 25 $\mu$C/g after charging, and presents a charge decay rate constant $Q_{50}$ of more than 0.1 s, a tap density of less than 0.8 g/ml and a water activity $a_w$ of less than 0.5.

Figure 2:
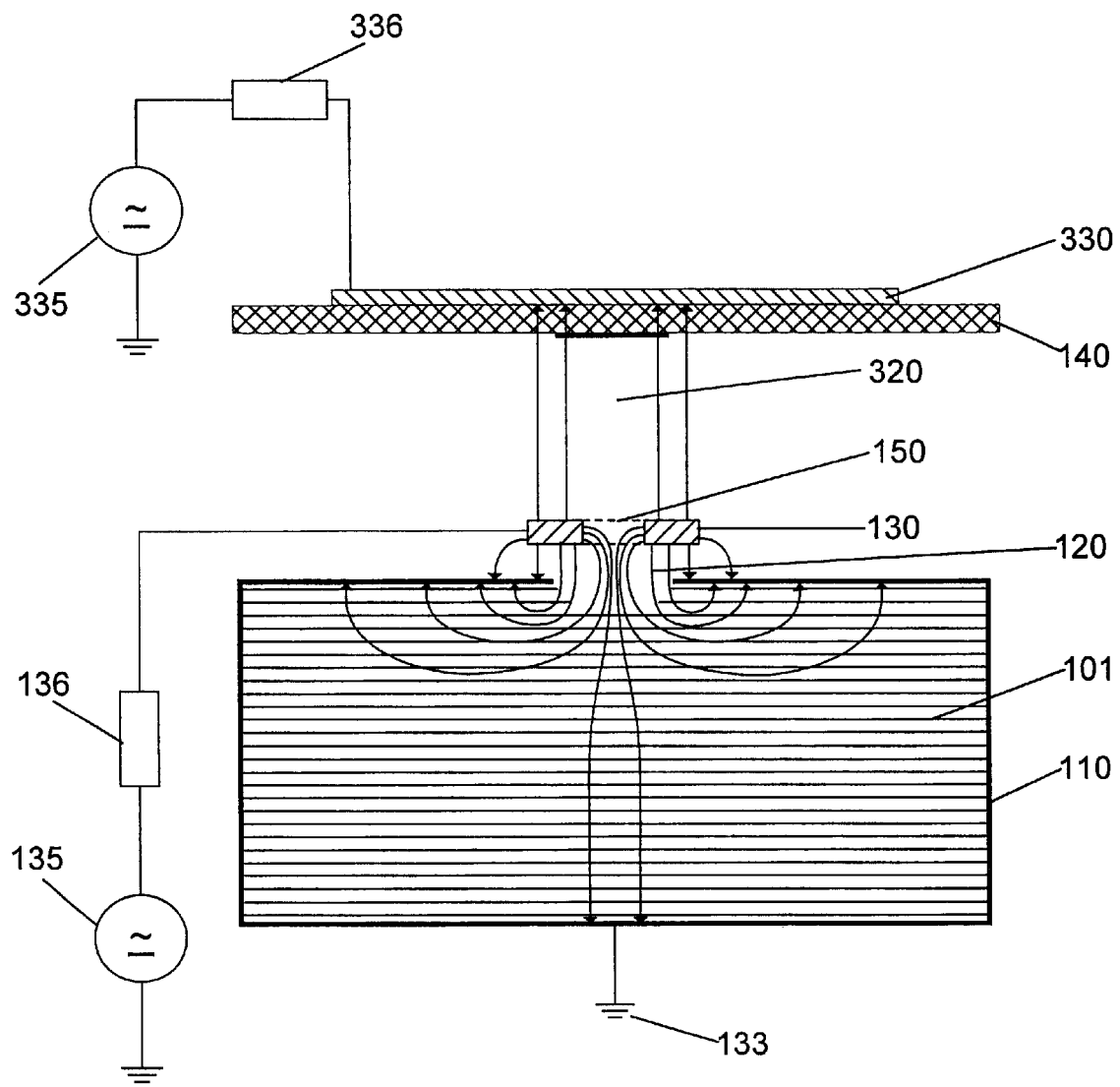

Taking reference in FIG. 1, particles 101 are released from the particle generator 110 provided with a positive or negative charge by corona-, tribo- or induction-charging, whereupon the particles enter an imposed first electric field 120. The type of charge of the particles depends on the powder characteristics, method of charging and materials in the generator so that the majority of the particles are charged either negatively or positively when they are emitted from the generator to take part in the dose forming process. In the following discussion and in the illustrations it is assumed that the emitted particles are positively charged. However, this depends on the properties of the powder and the generator and it is equally possible that the particles are negatively charged, in which case the applied potentials must change signs, but the discussion is still valid. In order to control the dose forming process in terms of total dose mass and dose forming time, the transfer of charged particles from the particle generator to the target area of the substrate member must be controlled. To this end, a first electric field is applied between ground 133 and a first electrode 130 connected to a first voltage source 135, including source impedance 136. The electrode is preferably positioned a short distance in the range 0.5–25 mm from the substrate member 140 between the particle generator 110 and the substrate member 140. The strength and direction of the created electric field 120 may be adjusted by adjusting the potential of the electrode within wide limits from a negative to a positive voltage, as set by the voltage source. Charged particles are thereby either attracted to (see FIG. 1) or repelled from (see FIG. 2) the first electrode, which has at least one aperture 150 of suitable size and shape where charged particles can pass through. Such apertures may be circular, elliptic, square or narrow slits or any other shape in order to suit the dose forming process. In a preferred embodiment, the aperture or apertures are in the range 50–5000 $\mu$m as main measures. However, particles attracted by the first electrode easily stick to it, which impairs the efficiency of the system and frequent cleaning may become necessary.

Figure 3:
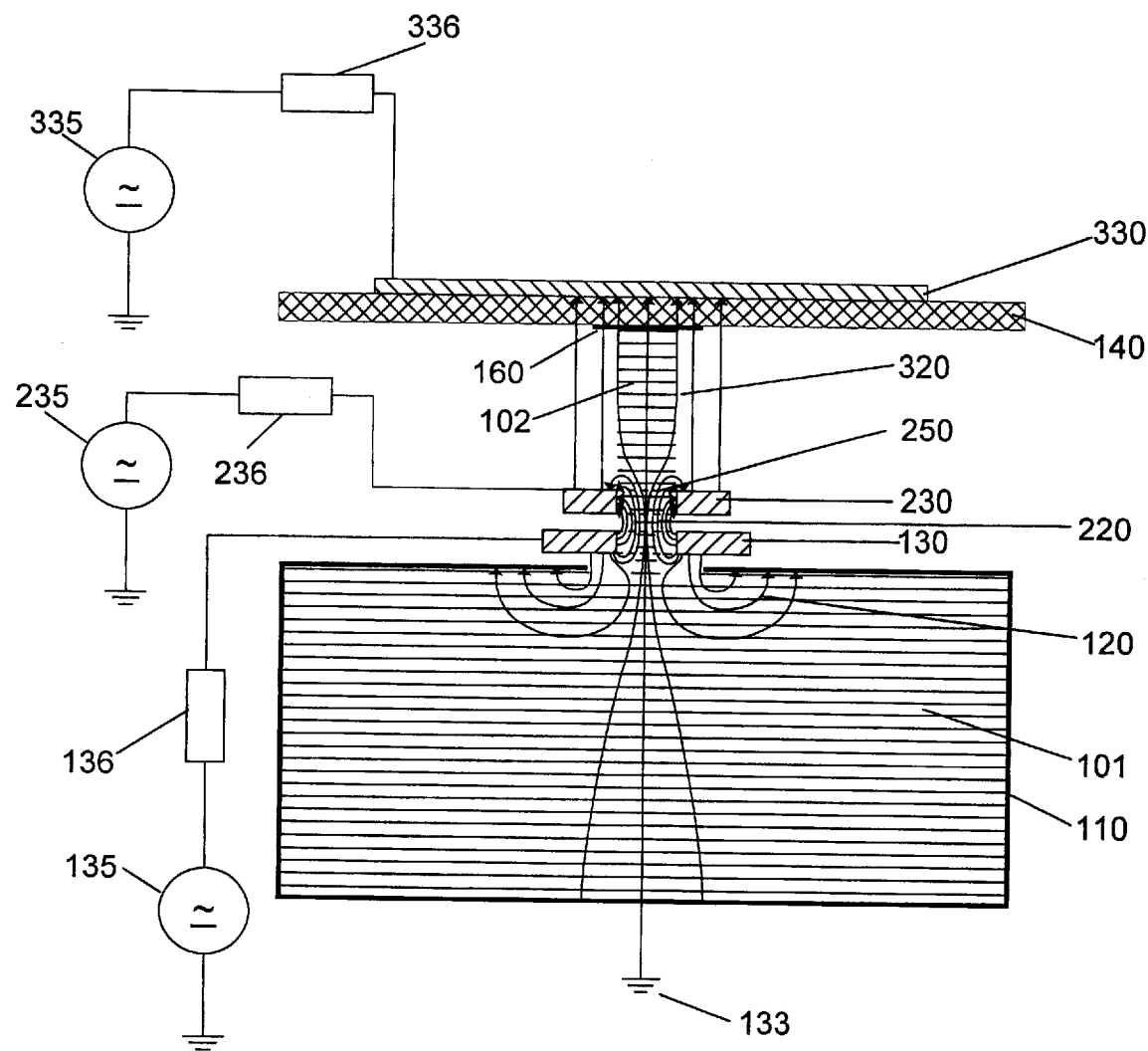
Figure 6:
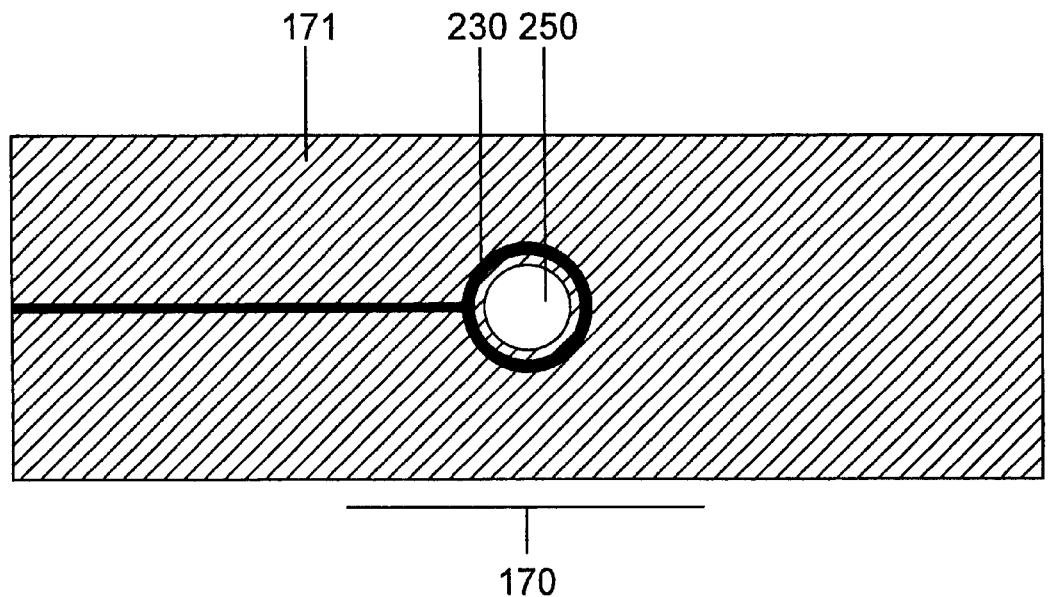

To eliminate the sticking effect and further improve the level of control of the transfer of particles to the target area of the substrate member, an optional second electrode 230 as illustrated in FIG. 3 and FIG. 6, may be introduced. It should be positioned in a plane parallel to the first electrode 130, in between the first electrode and the substrate at a distance between 0.07 and 2.5 mm from the first electrode. The second electrode is perforated by the same number of apertures 250 as the first electrode by using a layout, which matches the apertures 150 of the first electrode in position and shape such that the apertures of the two electrodes are concentric. The shape and size of the electrodes may vary from very large, comparable to the target area of the substrate member, to a fine circular ring less than 1 mm in diameter and less than 0.1 mm in width. Either the second electrode 230 may float electrically by not being connected to anything else or it may be connected to a second voltage source 235 with impedance 236. The strength and direction of a created second electric field 220 may be adjusted by adjusting the potential of the second electrode within wide limits from a negative to a positive voltage as set by the voltage source, if connected to the electrode. Charged particles 102 caught in the second field will travel along the field lines either in the direction of the second electrode or in the opposite direction, depending on the polarity of the applied voltage and hence the direction of the field lines.

Figure 4:
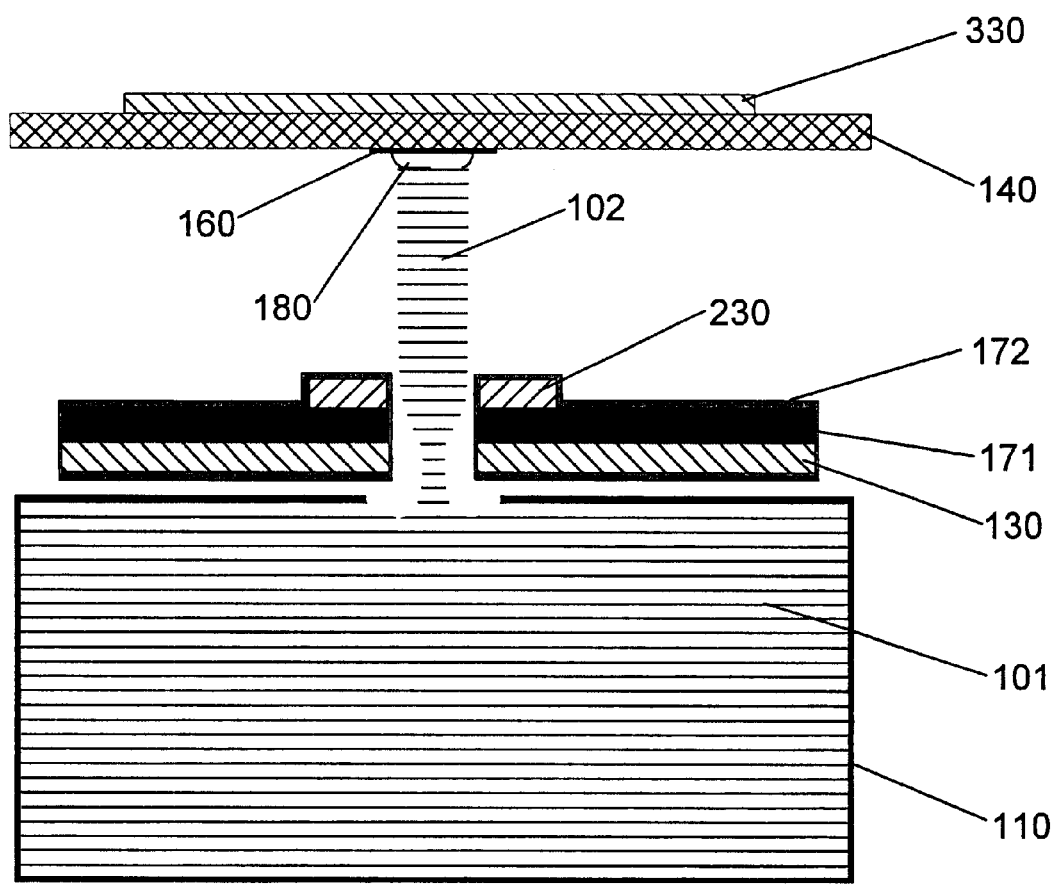

In a preferred embodiment, illustrated in FIG. 4, the first and second electrodes are integrated in an isolating wafer member 171 between the electrodes. The outward faces of the electrodes are preferably coated with an isolating coating 172 of a few microns in thickness, e.g. parylene, to stop possible short-circuiting of electrodes by sticking particles. The thickness of the wafer is typically in the range 0.07–2 mm. As an illustrative example the electrodes and the wafer member may be made as a printed circuit board. There are many types commercially available, e.g. in terms of number of possible conductor layers, physical flexibility and thickness.

Figure 5:
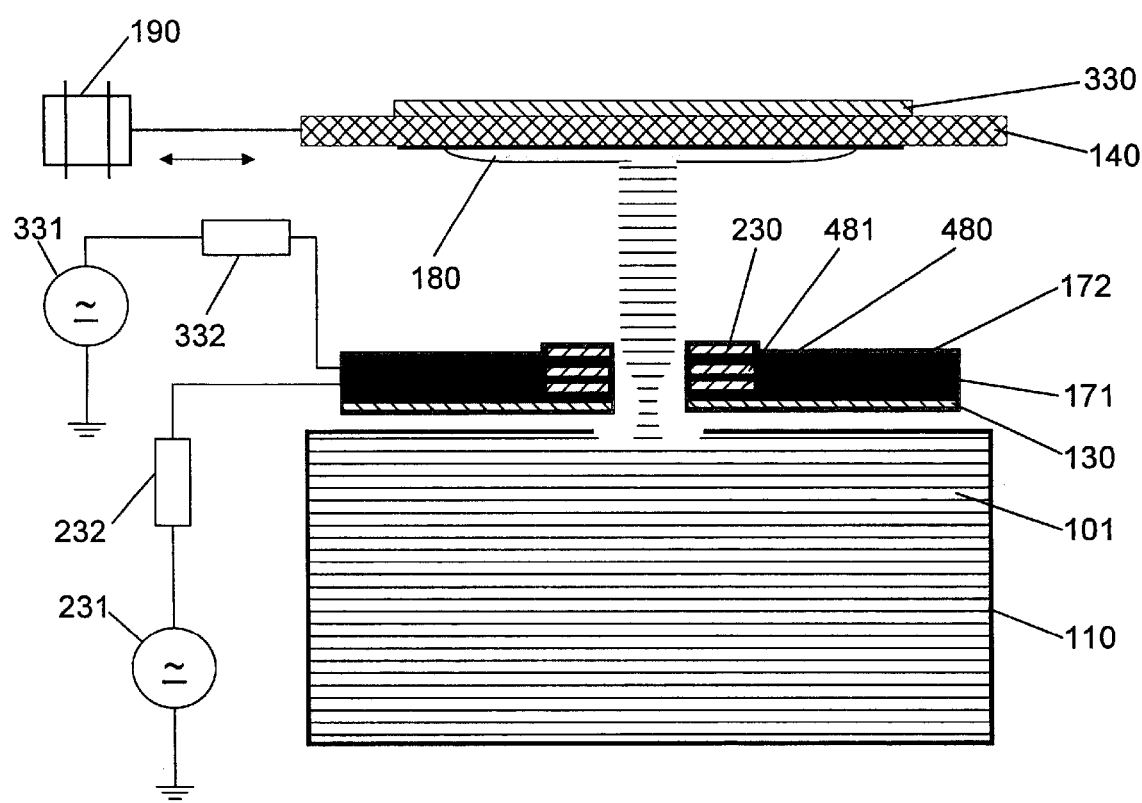

In further embodiments, as exemplified in FIG. 5, more electrodes 480, 481 may be introduced for specific purposes as, e.g. porosity control or screening of particles, which will be discussed separately. The extra electrodes 480, 481, if introduced, may be concentrically located either in extra layers of the isolating wafer member, or put in the same layer as the basic first and second electrodes. The extra electrodes are isolated from all other electrodes and ground to offer complete freedom in what connections to be made of electrodes to electric systems of controlled impedance and voltage sources. In this case the thickness of the wafer member may lie in the range 0.07–2.5 mm.

The wafer member 171 constitutes a physical barrier between the particle generator 110 and the substrate 140 with the dose bed that is the target area 160 for the deposition of charged particles 102. The distance between the top electrode or electrodes on the top of the wafer member and the substrate is in the range 0.5 to 25 mm. The only possibility for the particles to reach the dose bed is therefore to go through the available apertures of the first and second electrodes and possible extra electrodes, if introduced.

A further third electric field 320 is set up between ground 133 and a third electrode 330 connected to a third voltage source 335 (see FIG. 3). It is possible to reference the third voltage source to the output of the first or second electrode instead of ground to simplify control of the deposition process. The third electrode is preferably positioned in close proximity behind the substrate member 140 and the dose bed 160, such that the electric field lines go through the dose bed in the direction of the particle generator 110. The substrate member may be made of a dielectric or semiconductive material or even a conducting material or a combination of different such materials. In the case when the material in the dose bed is conductive, the dose bed may constitute the third electrode. The strength and direction of an ensuing third electric field 320 may be adjusted by adjusting the potential of the third electrode within wide limits from a negative to a positive voltage as set by the third voltage source, if connected to the electrode, such that the charged particles are either transported towards or away from the third electrode.

Figure 7:
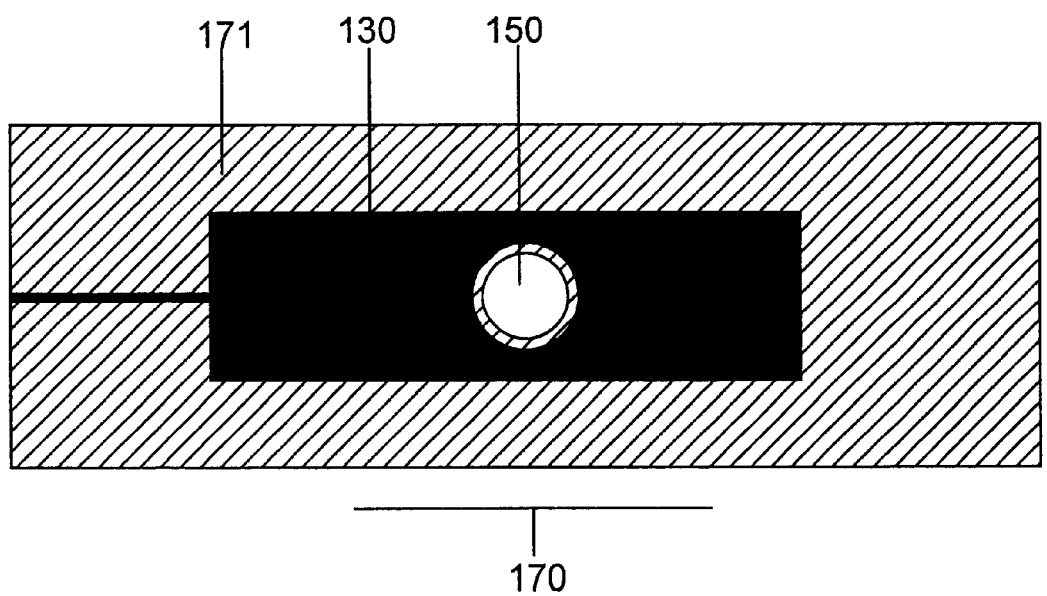

Charged particles 101 emitted from the generator 110 enter the combined electric field resulting from the potentials applied to the first, second and third electrodes respectively. The first electrode alone acts as an electric iris diaphragm device 170 and the addition of the optional second electrode improves the efficiency of the device considerably. A typical embodiment of the electric iris diaphragm is illustrated in FIGS. 6 and 7, showing the topside and bottom side respectively. It offers a possibility of controlling not only the particle transfer rate but also the apparent aperture size. The aperture or apertures through the first and second electrodes and through the isolating wafer, if present, can be made smaller or larger to the transported particles by increasing or decreasing the applied voltage potential of the first electrode while the potential of the second and third electrodes are kept constant. The electrode or electrodes, constituting the iris diaphragm, transfers charged powder particles 101, emitted from the generator, to the target area 160 on the substrate member in a controlled orderly way in terms of mass, direction and speed, like a printer ink-jet.

In a first aspect, the electric iris diaphragm 170 controls the area of the particle stream making it possible to control the physical size of the dose onto the target area. However, in a second aspect if the first potential is increased past a certain point, the exact voltage value at this point depends mainly on the relative strengths of the first, second and third electric fields, the iris diaphragm closes so that no particles are let through at all. This offers a simple way of instantaneous starting and stopping of the particle flow and may serve the purpose of tightly controlling the distribution and deposition of particles in the process of forming a preferred electro-dose most suitable for effective system delivery by inhalation.

By adjusting the second and third potentials fed to the respective electrodes, it is possible to partly control the transfer rate of particles through the aperture or apertures in the electrodes. In this third aspect the electric iris diaphragm acts as a particle flow control valve such that it is possible to adjust the amount of particles per unit time that are let through and consequently the deposition rate on the target area.

In a fourth aspect the electric iris diaphragm may be used to screen the particles such that only small particles 102 of preferred sizes are let through. This is achieved by superimposing an AC potential of suitable frequency and amplitude from a first AC source 231, as illustrated in FIG. 5, on e.g. the quasi-stationary second potential and, if necessary, from a second ac source 331 superimpose a second ac potential synchronized with the first ac potential on the quasi-stationary third potential. Another way of adding AC fields to the quasi-stationary fields may be the adding of special electrodes 480, 481 for the purpose and integrate the new electrodes in the same wafer element as the first and second electrodes and in line with these. In this case, the AC voltages are directly applied to the new electrodes instead of superimposed to the second and/or third electrode. The physical order of the electrodes may be interchanged to optimize the screening effect. The combined effect of the quasi-stationary fields taken together with the further superimposed AC fields is to accelerate the small and light particles to the dose bed on the substrate member but exclude the big and heavy particles. The working principle is based on the moment of inertia where big particles, i.e. agglomerates, have much more mass than small ones, but less charge per unit weight so that the former accelerate much more slowly in a given electric field compared to the latter. The frequency of the AC potentials are set so that heavy particles entering the second field, controlled by the second electrode, hardly oscillate in the field while the light particles oscillate with a larger amplitude such that the third field can take control of the particle at or just before it reaches the apex of the oscillation. The strength of the third electric field will at this point overcome that of the second field and the particle breaks loose to move in the direction of the third field leaving the second field. If the frequency of the AC field is suitable, the large particles will never travel through the iris diaphragm, but will stop in the iris diaphragm until they lose their charge so that the force of gravitation can bring them to a collection zone. These particles may then be recycled and further de-agglomerated and fed to the particle generator and re-introduced in the dose forming process. In this way the electro-dynamic field technique method further reduces the number of big particles being deposited and improves the quality of the dose.

After passing the iris diaphragm 170, the particles are accelerated in the third electric field, which may have an AC component, in the direction of the target area of the substrate member, i.e. the dose bed 160, under the attractive field force caused by the third field emanating from the third electrode behind the dose bed. The bed may be stationary or moving during the distribution of the particles. By utilizing a servomechanism 190, schematically illustrated in FIG. 5, the deposition of the particles can be controlled such that the spatial distribution of the particles on the dose bed area can be controlled arbitrarily.

For optimum performance when the dose 180 later is made available for inhalation, it is very important that the dose, besides consisting of small particles, also is provided with a desired porosity and structure. The porosity of the dose may be adjusted by suitably adjusting the amplitude and frequency of the second AC field superimposed on the quasi-stationary third field, which may also be adjusted suitably for the deposition process. It is also possible to adjust the porosity of the dose if the dose bed is subjected to high frequency vibration or a high frequency electric field, preferably after the distribution of particles has been completed. The porosity may be measured non-destructively by using e.g. existing, commercially available optical methods such as laser triangulation, automated image analysis or near-infrared analyzers (NIR) either during the deposition process or after the dose forming is finished. Measured data may then be used to continuously optimize the whole dose forming process on-line with the object to obtain a dose with suitable properties, preferably meeting the specification for an electro-dose. An electro-dose is defined as electrically dosed electro-powder using electric field techniques, the dose possessing following the specification: Porosity is defined as $$Dp_{electro-dose} = 100 - 100(\text{density}_{electro-dose}/\text{density}_{electro-powder\ substance}) > 75\%$$

In order to avoid that particles are deposited at random inside or even outside the target area, because of the local repelling electric field emanating from charges of already deposited particles, the charges must be neutralized during the dose forming process. In that case no significant local repelling electric fields will build up, which may distort the third electric field and weaken its attractive power, leading to a scattering of incoming charged particles. If charges accumulating in the dose and dose bed are frequently neutralized new particles will automatically go from the output of the iris diaphragm to the closest point of the dose bed such that there is a sharp distinction between the formed dose and the surrounding areas of the substrate.

Figure 8:
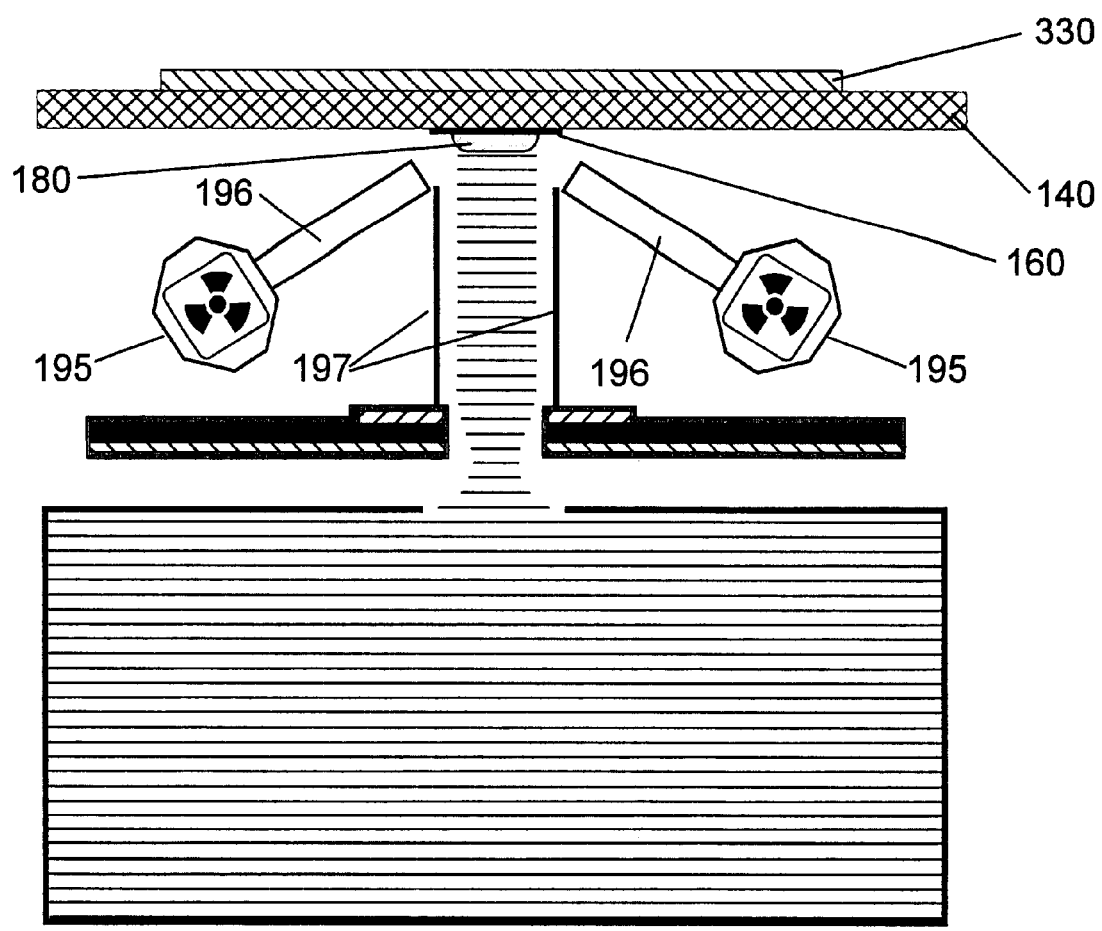
Figure 9:
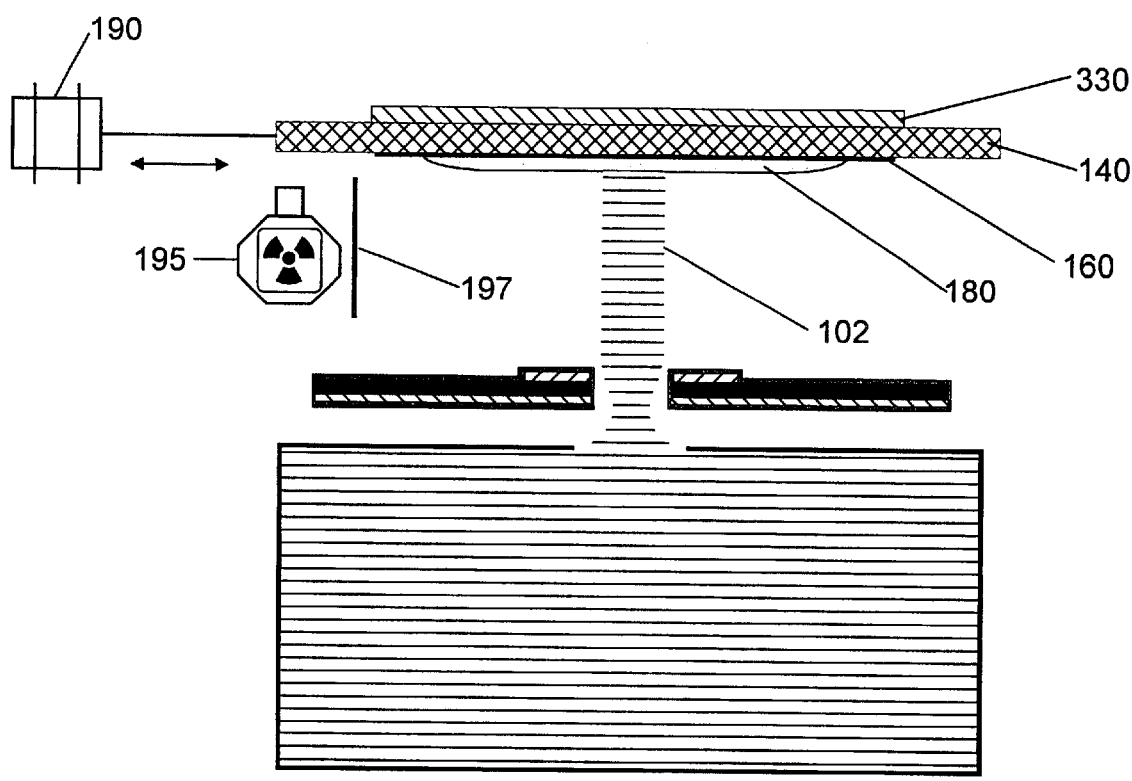
Figure 10:
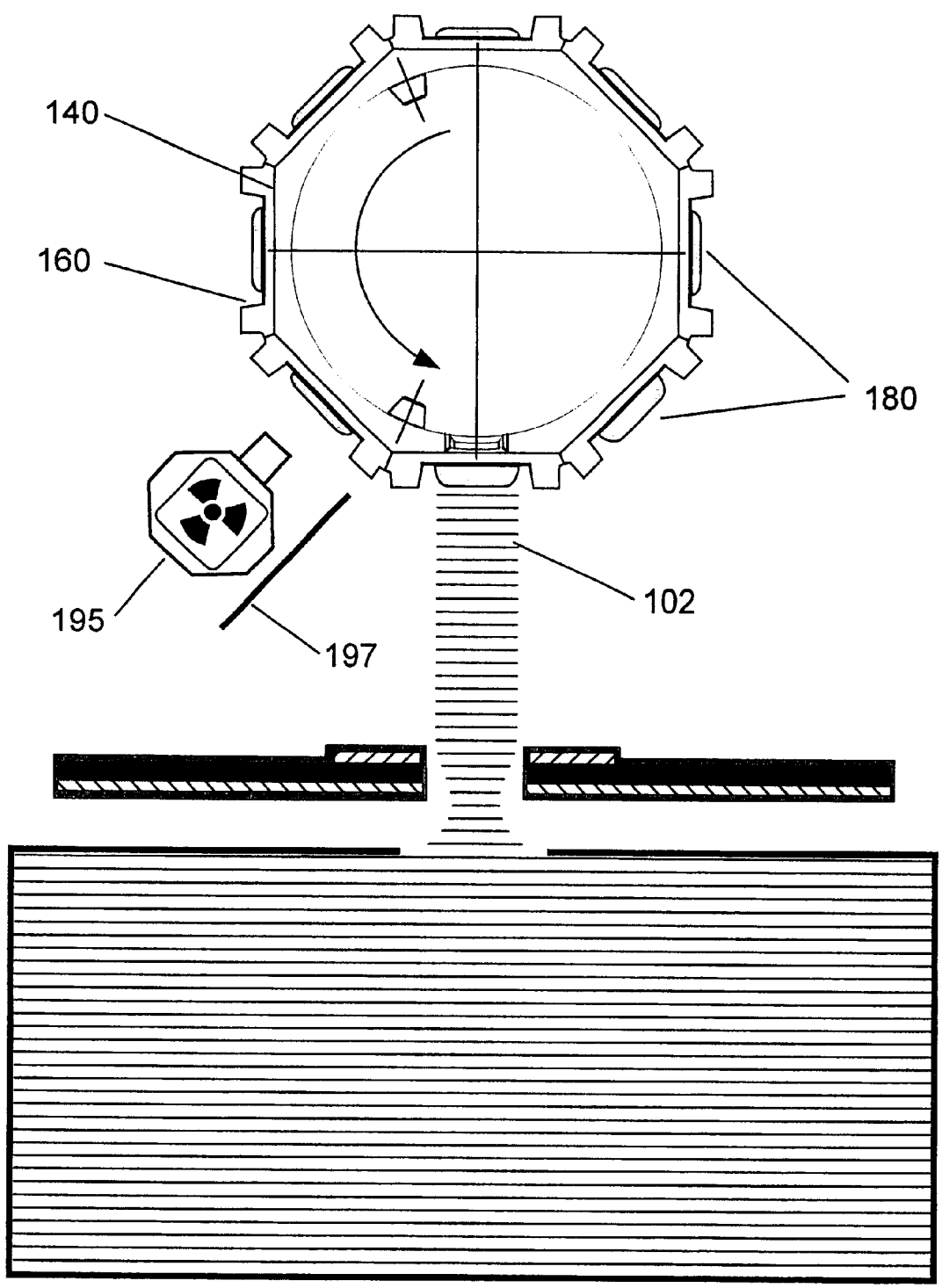

A key element of the invention is schematically illustrated in FIGS. 8, 9 and 10, i.e. the element neutralizing the accumulated charge of particles deposited on the dose bed. Various methods to remove charges may be used, but in a preferred embodiment a radioactive source 195 of alpha-particles (positively charged helium atoms) has been found to be most efficient. These sources are readily commercially available, e.g. from NRD LLC, Grand Island, N.Y. and are specifically used to discharge electrically charged objects.

The alpha particles are scattered uniformly in all directions from a point source and ionize the surrounding air creating both positive and negative ions. The new ions are attracted to oppositely charged particles and other charged objects in the vicinity and recombine to form regular atoms using the surplus charge of the objects with which they collide. The active range from the ion source is only a few centimeters. It is very easy to stop the alpha particles within the active range by putting any solid material in the way, like a sheet of paper. A preferred radioactive point source is model P-2042 Nuclespot™, which is based on Polonium-210, but other models are available to suit all kinds of applications. Polonium-210 is currently used and has a long record of use in all kinds of industry where static electricity is a problem. The radiation leaves no residue besides helium atoms (inert gas), which are the result of the alpha particles colliding with air molecules taking up two electrons from oxygen or nitrogen atoms. In their effort to recombine, a current of ions is established that quickly neutralizes charged objects and surfaces within the active range of the radioactive point source.

In one embodiment, illustrated in FIG. 8, it is possible to direct the alpha particles by designing at least one direction member 196 pointing to the spot on the dose bed where the powder particles 102 are deposited, such that immediately after the deposition the charge of the individual particles is neutralized. In a different embodiment, the ion source 195 is put outside the spot where the dose is formed, illustrated in FIG. 9. The previously mentioned servomechanism 190 is set up to withdraw the substrate 140 with the dose bed 160 after only a partial dose forming operation before too many particles 102 have been deposited and to neutralize charge in the dose bed and the dose 180 by exposing the substrate to the ion source. Yet another embodiment is illustrated in FIG. 10, showing a typical arrangement where the substrate member is a cassette 140 carrying at least one target area 160 for dose forming and an ion source directed towards the target area, which will receive the next dosing in a repeated sequence of dose forming operations.

For all embodiments it is generally necessary to include screens 197, which will absorb charges that otherwise risk interfering with charged particles while being transported in the electric fields set up to control the transport, distribution and final deposition of the particles in the dose forming process.

Figure 11:
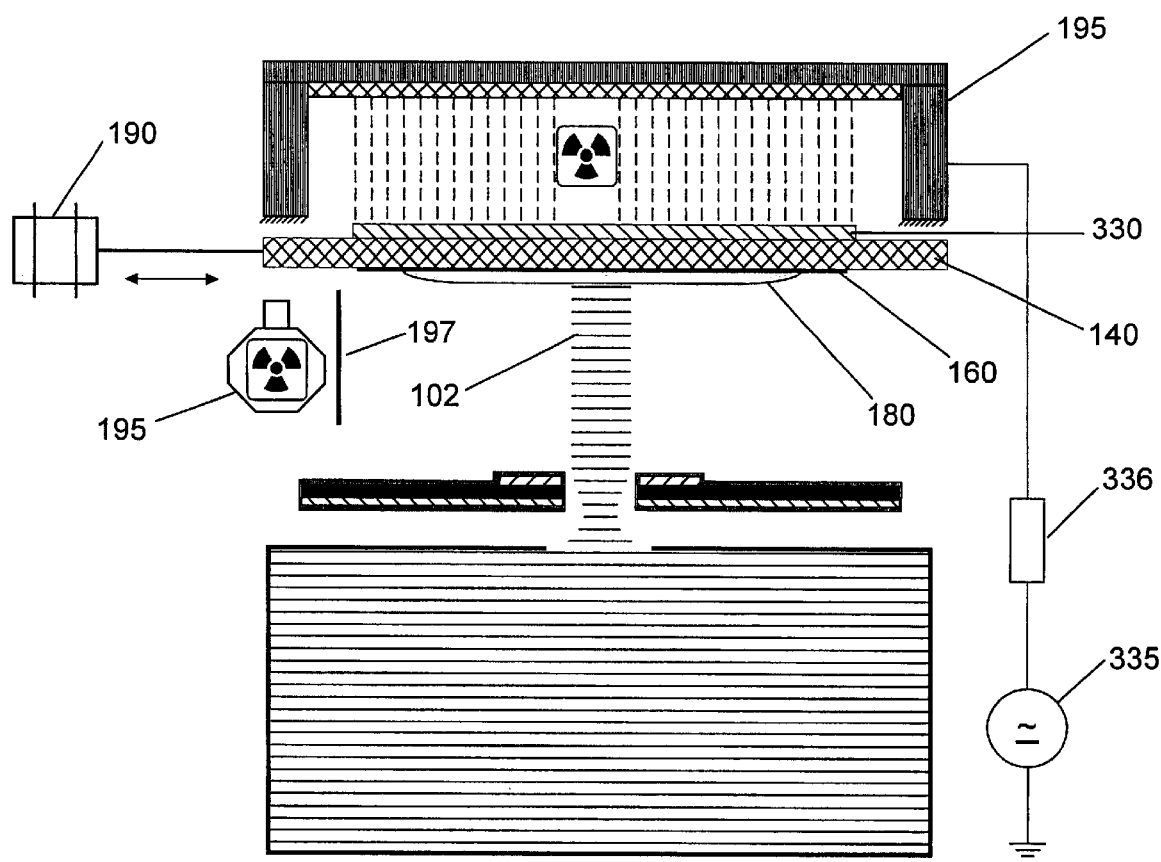

In a different embodiment physical constraints may exist in a member carrying one or more substrate members intended for doses, which make it difficult or impossible to arrange a contacting of an electrode behind the substrate member necessary for creating the third electric field as previously discussed. In such case, illustrated schematically in FIG. 11, a separate ion source 195 may advantageously be applied to make electrical contact with the third electrode 330 behind the substrate member 140 without actual physical contact. The emitted alpha particles ionize the air, which acts as an electric conductor between the ion source and the third electrode, which must be electrically conductive. The ion source should be of suitable size and placed within its working range 0–30 mm from the third electrode on the backside of the substrate member. If the metal shell of the ion source is connected to the third voltage source 335 with effective internal impedance 336, which now includes the impedance of the air gap, part of the applied voltage will also be present as a potential on the third electrode, such that the third field can be fully controlled.

It is worth noting that for all practical embodiments of the invention depositing large amounts of powder is no problem, provided the negative influence of the accumulated charge in the dose and on the substrate is removed by neutralizing the charges as described in the foregoing description. Then, the field strength from the third electrode is approximately constant through the substrate and developing dose. The distribution process and the forming of the dose are not sensitive to variations between particles in total charge or specific charge. As long as a particle has a charge of the right type and manages to pass the screening in the iris diaphragm, it will automatically be deposited onto the dose bed as long as the field exists. Provided suitable measuring instruments are put to use for monitoring the dose while it is formed, it is easy to control the described dose forming process on-line, using standard prediction, feed-forward or feed-back control methods, in combination if necessary.

Figure 12:
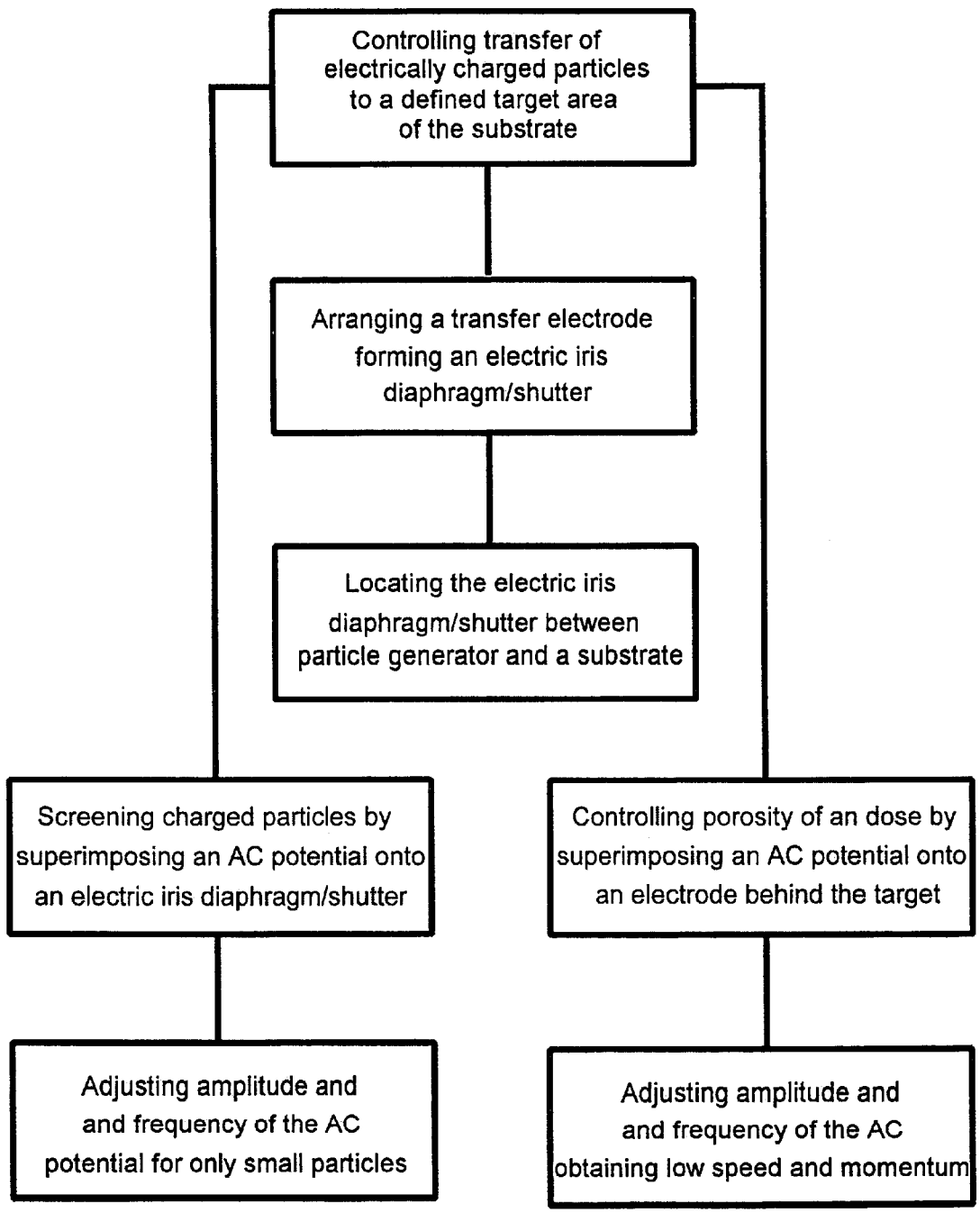

In a flow diagram in FIG. 12 the method of the present invention is briefly illustrated in accordance with the independent claims.

What has been said in the foregoing is by example only and many variations to the disclosed embodiments may be obvious to a person of ordinary skill in the art, without departing from the spirit and scope of the invention as defined in the appended claims.

What is claimed is:

1. A method for controlling transfer of electrically charged particles of a medication powder, intended for inhalation, emitted from a particle generator to a defined target area of a substrate member in a dose forming process, comprising the steps of arranging a particle transfer electrode member forming an electric iris diaphragm such that at least one electrode, being a part of said iris diaphragm with its associated electric field, operates to transfer charged particles emitted from said particle generator, to said defined target area of said substrate member, controlling the direction and speed of the particles, in the dose forming process, the charged particles being produced by one of corona-charging, tribo-charging, and induction charging;

locating said electric iris diaphragm between said particle generator and said substrate member such that all particles must pass the iris diaphragm in order to be transferred to the substrate member, the iris diaphragm being operable as a shutter.

2. The method according to claim 1, comprising the further step of making an electric iris diaphragm comprising an isolating wafer member and at least one electrode for controlling on one hand transfer of charged particles through the at least one aperture and on the other hand distribution of particles on a target area of the substrate member.

3. The method according to claim 2, comprising the further step of using a flexible or rigid printed circuit board as the iris diaphragm.

4. The method according to claim 1, comprising the further step of positioning the substrate member at a distance of 0.1–5 mm from the top of said electric iris diaphragm to said substrate member.

5. The method according to claim 1 comprising the further step of applying quasi-stationary potentials to electrode members forming the electric iris diaphragm to switch a flow of charged particles on or off in said dose forming process.

6. The method according to claim 1, comprising the further step of applying quasi-stationary potentials to electrode members forming the electric iris diaphragm to adjust a mass flow per unit time of charged particles in said dose forming process.

7. The method according to claim 1, comprising the further step of applying quasi-stationary potentials to electrode members forming the electric iris diaphragm thereby controlling the size of the aperture of the iris diaphragm setting an area of the flow stream of charged particles in said dose forming process.

8. The method according to claim 1, comprising the further step of frequently neutralizing electrical charge from a dose and said substrate member by introducing equalizing charges from a source member such that a repelling electric field from deposited particles is nullified.

9. The method according to claim 1, comprising the further step of using an ion source to make electric contact without physical contact with an electrode on the back side of said substrate member in order to connect a controlled potential to an electrode thus creating a necessary electric field emanating from said electrode for the transportation of the charged particles to the target area in said dose forming process.

10. A method for controlling transfer of electrically charged particles of a medication powder, intended for inhalation, emitted from a particle generator to a defined target area of a substrate member in a dose forming process, comprising the steps of screening electrically charged particles of a medication powder during a dose forming process by superimposing an AC potential onto an existing quasi-stationary potential on at least one electrode of electrodes forming an electric iris diaphragm;

adjusting amplitude and frequency of said AC potential such that small, light, charged particles will oscillate in an AC field created, such that only particles having aerodynamic sizes less than 5 $\mu$m emerge from said iris diaphragm to be further transferred in the dose forming process, the iris diaphragm being operable as a shutter.

11. A method for controlling transfer of electrically charged particles of a medication powder, intended for inhalation, emitted from a particle generator to a defined target area of a substrate member in a dose forming process, comprising the steps of controlling porosity of a dose of said medication powder while it is being formed in the dose forming process by superimposing an AC potential on an existing quasi-stationary potential on an electrode behind the defined target area of said substrate member where powder particles comprising a dose are to be distributed in the dose forming process;

adjusting amplitude and frequency of said AC potential such that a majority of charged particles emerging from an electric iris diaphragm are accelerated and retarded in synchronism with an AC field created, such that they impact on said defined target area of said substrate member with a speed and momentum resulting in an intended dose porosity, the iris diaphragm being operable as a shutter.

* * * * *